United States Patent [19]
Goettsch et al.

[11] 3,944,543
[45] Mar. 16, 1976

[54] PROCESS FOR RECOVERY OF ε-CAPROLACTAM

[75] Inventors: Reijer Goettsch, Beek; Abraham H. De Rooij, Geleen, both of Netherlands

[73] Assignee: Stamicarbon, B.V., Geleen, Netherlands

[22] Filed: June 11, 1974

[21] Appl. No.: 478,331

[30] Foreign Application Priority Data
June 12, 1973 Netherlands.................... 7308100

[52] U.S. Cl........................................ 260/239.3 A
[51] Int. Cl.$^2$................................... C07D 201/16
[58] Field of Search............................ 260/239.3 A

[56] References Cited
UNITED STATES PATENTS

| | | | |
|---|---|---|---|
| 2,221,369 | 11/1940 | Cass............................ | 260/239.3 A |
| 2,758,991 | 8/1956 | Kretzers et al............... | 260/239.3 A |
| 3,336,298 | 8/1967 | De Rooij...................... | 260/239.3 A |
| 3,852,272 | 12/1974 | De Rooij...................... | 260/239.3 A |
| 3,852,273 | 12/1974 | De Rooij...................... | 260/239.3 A |

*Primary Examiner*—Henry R. Jiles
*Assistant Examiner*—Robert T. Bond
*Attorney, Agent, or Firm*—Cushman, Darby & Cushman

[57] ABSTRACT

Polymerizable quality ε-caprolactam having an alkalinity of less than 0.05 meq. per kg. of lactam is produced in the improved disclosed process which includes extracting an aqueous lactam-rich solution with an organic solvent having a high distribution coefficient for the lactam with respect to the aqueous solution, and evaporating the lactam-rich organic solvent solution and recovering by distillation the lactam. Evaporation of the organic solvent requires considerably less thermal energy than evaporation of a similar aqueous solution.

3 Claims, 2 Drawing Figures

PROCESS FOR RECOVERY OF ε-CAPROLACTAM

BACKGROUND OF THE INVENTION

This invention relates to the recovery of ε-caprolactam, as described, amongst others, in the Netherlands Patent Applications 7,106,341 and 7,106,343. According to these processes ε-caprolactam is extracted using a water-immiscible organic solvent for the lactam from a lactam-containing starting solution which is still highly acid. The starting solution is obtained by neutralizing about half of the sulfuric acid content in a rearrangement mixture containing lactam and sulfuric acid with the aid of ammonia water or an ammonium sulfate solution which forms an aqueous solution which, in addition to the lactam, mainly contains ammonium hydrogen sulfate and possibly a small amount of free sulfuric acid or ammonium sulfate, depending on the degree of neutralization of the rearrangement mixture. The organic solvent is freed from lactam by evaporation and back-extraction with water and the organic solvent is again used for the extraction of lactam from the highly acid starting solution.

Processing of the thus-obtained lactam in water solution is additionally conducted in the usual way by evaporation of water, first at atmospheric pressure until a concentration of approximately 90% by weight of lactam has been reached, and subsequently under vacuum conditions to evaporate the remaining water.

For further purification of the product it is customary to have the lactam distil over in vacuo. Although the lactam reocvered in this way already of sufficient purity to satisfy various strict specification demands made on lactam intended for polymerization into nylon, such as requirements in relation to the melting point, color, clearness and permanganate number, even so the thus-treated lactam generally does not satisfy the customary alkalinity requirement.

This requirement specifies that the alkalinity, expressed in meq per kg of lactam, shall be below 0.05. The alkalinity is determined by dissolving 40 grams of lactam in distilled water, then increasing the volume to 200 ml and titrating the solution with 0.01 N of hydrochloric acid in the presence of a mixing-indicator which changes in the pH range of 5–6; preferably the "Tashiro" indicator is used.

In the lactam recovered in the manner described above, starting from different samples of lactam-sulfuric acid rearrangement mixture, invariably an alkalinity of more than 0.05 and generally an alkalinity as high as about 0.1 was found.

DETAILED DESCRIPTION OF THE INVENTION

We have now found that the alkalinity of the lactam can be reduced to the required value, that is 0.05 meq per kg of lactam, in a simple, expedient manner by extracting the aqueous solution of lactam with a water-immiscible organic solvent thereby forming a solution of lactam in the organic solvent from which the lactam is subsequently recovered by evaporation of the solvent and the lactam is then distilled over in vacuo in the usual way.

Conditions during the back extraction step are similar to those in the extraction step preceeding it, that is at temperatures of the order of about 20° to about 50° C, conveniently at about ambient temperature, and under atmospheric pressure. The use of higher or lower pressures gives no particular advantage. Similarly conditions in the evaporating step are also related to prior procedures, except that somewhat lower temperatures are used, i.e. 60° to 80° C, owing to the lower boiling point of the organic solvent as compared to water, and the thermal energy requirement is significantly less, as explained below.

According to our experiences all test quantities of lactam produced this way satisfied the requirement of an alkalinity of less than 0.05 meq per kg of lactam and were acceptable for polymerization into nylon according to known procedures.

Not only does the back-extraction or lactam from the aqueous lactam solution using a water-immiscible organic solvent result in a product of acceptable, saleable alkalinity, but this procedure inherently provides further advantage and that is a decrease of the processing costs.

If back-extraction as described herein is not carried out all water must be removed, usually evaporated, from the aqueous lactam solution, which prior to removal generally has a lactam content of 30–35% by weight. In view of the high evaporation heat of water (540 kcal/kg), the evaporation step by itself requires a considerable amount of energy. On the other hand and according to the procedures described herein, if instead of water one uses a suitable organic solvent having a much lower evaporation heat, like chloroform (evaporation heat 59 kcal/kg), must be evaporated as a result of the back-extraction, a substantial saving on the evaporation cost is obtained, as simply less thermal energy is required to accomplish the same result. For instance, in the evaporating of the water and chloroform from an aqueous lactam solution containing 30% by weight of lactam and 2% by weight of chloroform, 1260 keal are necessary per kg of lactam; however, by back-extraction with chloroform a solution of 35% by weight of lactam and 3.8% by weight of water in chloroform is formed. Overall the evaporation of the chloroform and water requires 167 keal per kg of lactam, thus a substantial savings is obtained as the thermal energy required is only one-tenth that of the aqueous-based solution.

Figure 1:
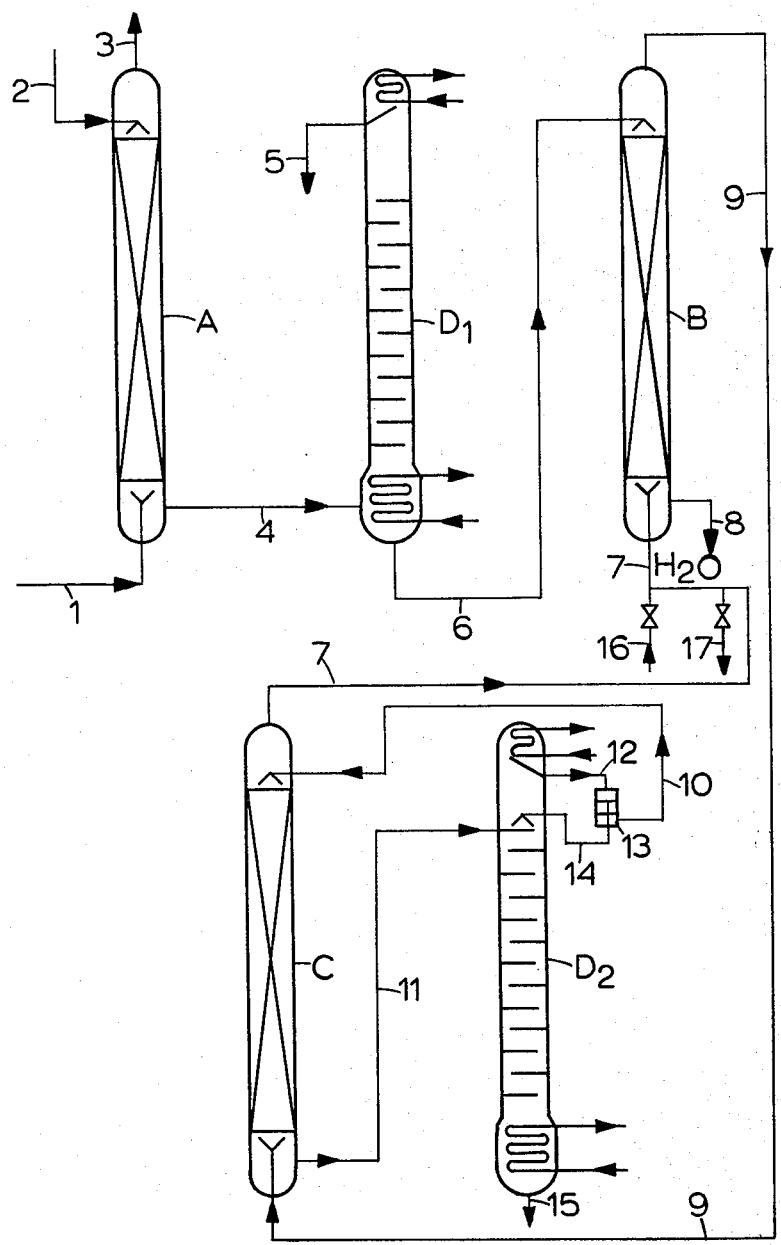
Figure 2:
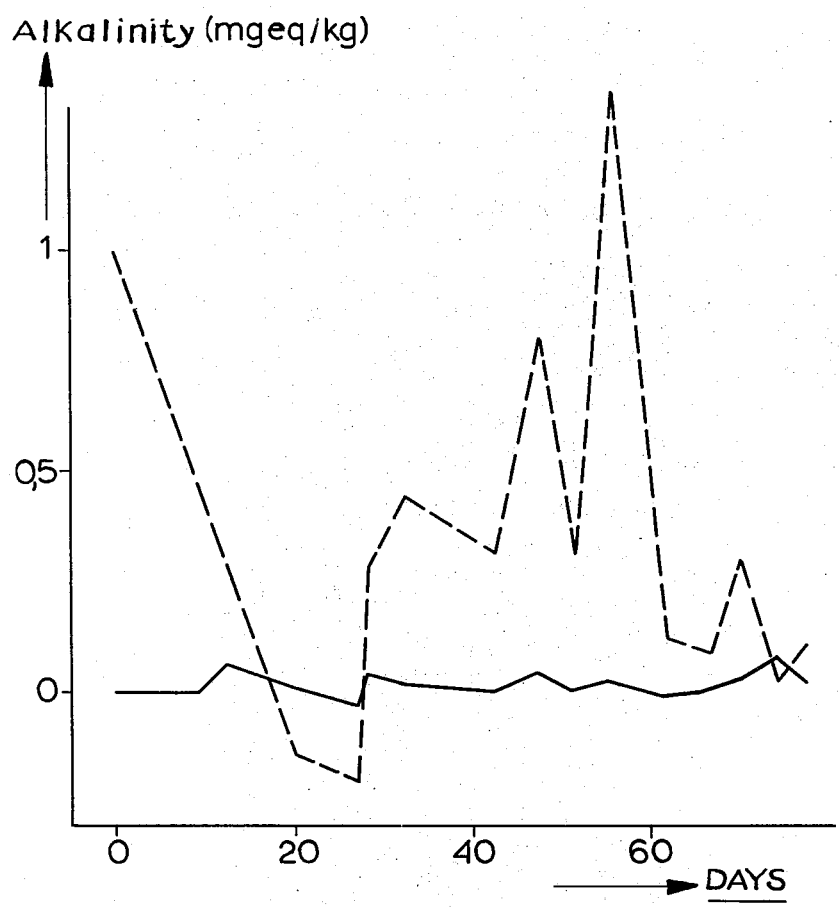

FIG. 1 is a schematic illustration of one manner of conducting the process of the present invention; and FIG. 2 is a graph plotting alkalinity, in meq/kg, of lactam against time in days. The solid line is according to the example while the interrupted or dashed line is comparison.

One manner of conducting the process of the present invention is illustrated schematically in FIG. 1, in which A, B and C represent extraction columns. Although this represents a preferred embodiment other arrangements can, of course, be made. For instance instead of packed extraction columns other extraction equipment may also be used, the so-called RDC columns for instance. $D_1$ and $D_2$ represent distillation columns.

A partially (50%) neutralized rearrangement mixture — actually a solution of lactam and ammoium hydrogen sulphate in water — is supplied via line 1 to column A, to be extracted countercurrently in column A with an organic solvent, for instance chloroform, supplied via line 2. A solution of ammonium hydrogen sulphate free from lactam is discharged via line 3, while the remaining solvent rich in lactam and also containing dissolved water and sulfuric acid is directed into distillation column $D_1$ via line 4 after neutralization of the sulfuric acid (not shown), the solvent being concentrated in the distaillation column. That portion of the solvent distilled off condenses in the top part of $D_1$ on the cooling coils, the condensate is discharged via line 5 and — after water which has also been distilled over has been separated off — is recycled and again used for the extraction. The concentrated lactam solution is directed into extraction column B via line 6, in which column back-extraction of lactam takes place with the aid of water supplied via a line 7. Solvent which is virtually free from lactam is discharged via line 8, to be again used as the extraction agent for removal of lactam from the partially neutralized rearrangement mixture.

From the top of column B the solution of lactam in water obtained is directed via line 9 to extraction column C where back-extraction of lactam takes place with the aid of an organic solvent supplied via line 10. Water freed from lactam is recycled via line 7, and the solvent loaded with lactam and small quantities of water is led via line 11 into distillation column $D_2$, where the solvent is distilled off and discharged as condensate via line 12. Water which is also distilled over will settle in separator 13 and be returned as reflux to column $D_2$ via line 14. The organic solvent which is freed from water is returned to the extraction column C via the line 10 and recycled.

From the bottom part of distillation column $D_2$ a lactam melt containing water is then directed via a line 15 to a conventional distillation apparatus (not illustrated), where water is removed in vacuo and, again in vacuo, lactam is distilled and recovered over.

In view of the fact that during the treatment steps described above the extraction water is kept in continuous circulation via line 7, column B, line 9, column C and, again, line 7, impurities washed out of the lactam are accumulated in the extraction water circulation system. For this reason the system is provided with a supply line 16 for fresh water and with a discharge line 17, so that, if necessary, contaiminated water may be periodically or continuously replaced as desired.

It is possible to use and organic extraction agent in extraction column C different from that used in column A however this does not offer any particular advantage and indeed in order for the operational control to be maintained in a direct and simple manner it is preferable as a practical matter, to use the same organic solvent in the initial extraction in column A and in the back-extraction in column C.

In view of the acid character of the lactam-containing aqueous starting solution, the solvent employed must have a very favorable distribution coefficient for lactam with respect to water such as a distribution coefficient in the order of 1 to 2 or so. Moreover, in connection with the subsequent removal of the solvent by distillation, a relatively low boiling point is desirable, that is an organic solvent boiling at about 60° to about 80°C.

Chlorinated hydrocarbons selected from the group of chloroform, methylene chloride and 1-2 dichloroethane satisfy both demands and are thus the preferred solvents.

The process of the present invention is now described in more detail as a further illustration of the process. Unless otherwise indicated all parts and percentages are by weight.

EXAMPLE

Into an apparatus arrangement illustrated in FIG. 1 with a capacity of about 3 kg of lactam per hour a solution obtained by the known Beckmann rearrangement of cyclohexanone oxime and neutralization of the so-obtained rearrangement mixture is directed continuously via line 1, in a quantity of 13 kg per hour. This solution contains 3.39 kg of lactam. Via the line 2, 10 kg of chloroform per hour are introduced. At the bottom of the column A a 24.2% by weight solution of lactam in chloroform is obtained, which is concentrated in the distillation column $D_1$; 5.7 kg of a 60% by weight solution of lactam (5.7 kg) in chloroform is obtained, which is extracted with water (8 kg) in column B, with the formation of aqueous solution (11.66 kg) containing 29.6% by weight of lactam and 2% by weight of chloroform.

The lactam contained in this squeous solution is back-extracted with chloroform (8 kg) in column C; 11.9 kg of solution with 28.6% by weight of lactam and 3% by weight of water are obtained and further processed in vacuo in the manner described above in non-drawn columns.

The measured alkalinity of the lactam so produced is reported on the graph of FIG. 2 and indicated by the solid line, covering a period of 120 days; the interrupted or dashed line is a comparison and represents the alkalinity of lactam recovered from samples of aqueous solution drawn out of line 9, which means samples that have not been subjected to back-extraction. Accordingly these values are for comparative purposes and not according to the present invention.

No additional extraction water was supplied to the system during the first 70 days of this continuous test.

What is claimed is:

1. In a process for the purification and recovery of ε-caprolactam monomer of reduced alkalinity content including the steps of neutralizing a rearrangement mixture of the lactam and sulfuric acid to form an aqueous solution of lactam and ammonium hydrogen sulfate, extracting the lactam from the mixture with a water-immiscible organic solvent for the lactam, extracting the lactam/organic solvent solution with water to form an aqueous solution of lactam, the improvement comprising extracting the thus-obtained aqueous lactam-rich solution with a water-immiscible organic solvent having a high distribution coefficient for the lactam with respect to the water of the aqueous solution forming a solution of the lactam in the organic solvent and thereafter evaporating the lactam-rich organic solvent and thereby recovering the purified lactam from the evaporation of the organic solvent, the thus-recovered lactam having an alkalinity of less than 0.05 meq. per kg of lactam.

2. The process according to claim 1 wherein the solvents used in both extraction steps are the same.

3. The process according to claim 1 wherein the extraction solvent of step (1) is a chlorinated hydrocarbon selected from the group consisting of chloroform, methylene chloride and 1,2-dichloroethane.

* * * * *